(12) United States Patent
Eggenspieler et al.

(10) Patent No.: US 8,006,539 B2
(45) Date of Patent: Aug. 30, 2011

(54) ACTUATION SYSTEM

(75) Inventors: Damien Eggenspieler, Paris (FR);
Devvrath Khatri, Pasadena, CA (US);
Chiara Daraio, Pasadena, CA (US)

(73) Assignee: California Institute of Technology,
Pasadena, CA (US)

( * ) Notice: Subject to any disclaimer, the term of this patent is extended or adjusted under 35 U.S.C. 154(b) by 409 days.

(21) Appl. No.: 12/364,974

(22) Filed: Feb. 3, 2009

(65) Prior Publication Data
US 2009/0199643 A1    Aug. 13, 2009

Related U.S. Application Data

(63) Continuation-in-part of application No. 12/251,164, filed on Oct. 14, 2008.

(60) Provisional application No. 61/063,903, filed on Feb. 7, 2008, provisional application No. 61/124,920, filed on Apr. 21, 2008, provisional application No. 61/135,266, filed on Jul. 18, 2008.

(51) Int. Cl.
*G01M 7/08* (2006.01)
*G01N 3/34* (2006.01)
*G01N 33/38* (2006.01)
*G01N 3/303* (2006.01)

(52) U.S. Cl. ...................................... 73/12.11; 73/12.13

(58) Field of Classification Search ................. 73/11.01, 73/11.02, 12.01, 12.02, 12.04, 12.05, 12.06, 73/12.11, 12.13, 12.14
See application file for complete search history.

(56) References Cited

U.S. PATENT DOCUMENTS

| | | | |
|---|---|---|---|
| 2,729,094 A * | 1/1956 | Piety | 73/1.85 |
| 3,724,260 A * | 4/1973 | Bole | 73/12.13 |
| 4,116,041 A * | 9/1978 | Tholen et al. | 73/12.13 |
| 4,711,754 A | 12/1987 | Bednar | |
| 5,165,270 A | 11/1992 | Sansalone | |
| 5,497,649 A * | 3/1996 | Ambur et al. | 73/12.06 |
| 5,736,642 A | 4/1998 | Yost | |
| 5,841,019 A | 11/1998 | Drabrin | |
| 6,418,081 B1 | 7/2002 | Sen | |
| 6,799,126 B1 | 9/2004 | Ratcliffe | |
| 6,843,957 B2 | 1/2005 | Statnikov | |
| 7,191,656 B2 * | 3/2007 | Yagi et al. | 73/579 |
| 2005/0072236 A1 | 4/2005 | Heyman | |
| 2006/0144146 A1 | 7/2006 | Hedberg | |
| 2006/0207913 A1 | 9/2006 | Hong | |

(Continued)

FOREIGN PATENT DOCUMENTS
WO    2007/084318    7/2007

OTHER PUBLICATIONS

McCracken, Jennifer et al. "S.R.-22 Smart Pavement: Response Characteristics of a Jointed Plain Concrete Pavement to Applied and Environmental Loads," University of Pittsburgh, (Feb. 2008).

(Continued)

*Primary Examiner* — Hezron E Williams
*Assistant Examiner* — Rose M Miller
(74) *Attorney, Agent, or Firm* — Steinfl & Bruno LLP

(57) ABSTRACT

A method and system for creating highly nonlinear solitary waves for use in performing nondestructive evaluation of structures and materials. The method and system use an apparatus having a spring loaded adjustable striker, a chain of granular particles, and a reloading device that allows for repeated activation of the adjustable striker.

24 Claims, 9 Drawing Sheets

U.S. PATENT DOCUMENTS

2006/0225509 A1  10/2006  Haupt

OTHER PUBLICATIONS

Daraio, C.; Nesterenko, V.F.; Herbold, E., and Jin, S. "Pulse mitigation by a composite discrete medium". *Journal De Physique IV Proceedings DYMAT 2006. 8th International Conference on Mechanical and Physical Behavior of Materials under Dynamic Loading*, J. Phys. IV France 134,473-479, Dijon, France (2006).

Grote, K., Hubbard, S., Harvey, J., and Rubina, Y., "Evaluation of infiltration in layered pavements using surface GPR reflection techniques," *Journal of Applied Geophysics* 57 (2005) 129-153 (2005).

Lanza di Scalea, F., Rizzo, P., and Seible F., "Stress Measurement and Defect Detection in Steel Strands by Guided Stress Waves," *ASCE Journal of Materials in Civil Engineering*, vol. IS (3), pp. 211-304 (2003).

Nesterenko, V.F.; Lazaridi, A.N. and Sibiryakov, E.8. The decay of soliton at the contact of two "acoustic vacuums". *Prikl. Mekh. Tekh. Fiz*. 2, 19-22 (1995) [*J. Appl. Mech. Tech. Phys*. 36, 166-168 (1995)].

Tinkey, Y., and Olson, L.D. "Non-Destructive Evaluation Method for Determination of Internal Grout Conditions Inside Bridge Post-Tensioning Ducts Using Rolling Stress Waves for Continuous Scanning," *NCHRPIDEA Program Project Final Report, Publisher: Transportation Research Board*, http://pubsindex.trb.org/documentlview/default.asp?Ihid=80 1832). (2007).

M Sansalone, N. J Carino, *Impact-Echo: A Method for Flaw Detection in Concrete Using Transient Stress Waves*, NBSIR 86-3452, National Bureau of Standards, (NTIS PB 87-1044441 AS). (1986).

Del Duce, A. and Kiliey, R.I. Comparison of Nonlinear Pulse Interactions in 160-Gb/s Quasi-Linear and Dispersion Managed Soliton Systems. Journal of Lightwave Technology, vol. 22, No. 5, pp. 1263-1271 (2004).

Daraio, C., Nesterenko, V.F., "Highly nonlinear contact interaction and dynamic energy dissipation by forest of carbon nanotubes," *Applied Physics Letters*, vol. 85, No. 23, pp. 5724-5726 (Dec. 7, 2004).

PCT International Search Report for PCT/US2009/032954 filed on Feb. 3, 2009 in the name of California Institute of Technology et al.

PCT Written Opinion for PCT/US2009/032954 filed on Feb. 3, 2009 in the name of California Institute of Technology et al.

PCT International Search Report for PCT/US2008/079860 filed on Oct. 14, 2008 in the name of California Institute of Technology et al.

PCT Written Opinion for PCT/US2008/079860 filed on Oct. 14, 2008 in the name of California Institute of Technology et al.

Arancibia-Bulnes, C.A. and Ruiz-Suarez, J.C. Broad solitons in homogeneous Hertzian granular chains, Physica D, 168, pp. 159-160, (2002).

Benson, D.J., Nesterenko, V.F. Anomalous decay of shock impulses in laminated composites, Journal of Applied Physics, 89, pp. 3622-3626, (2001).

Coste, C. and Gilles, B. On the validity of Hertz contact law for granular material Acoustics, European Physical Journal B, 7, 155 (1999).

Coste, C., Falcon, E., & Fauve, S. Solitary waves in a Chain of Beads under Hertz contact, Phys. Rev. E, 56, 6104-6117 (1997).

Daraio, C.; Nesterenko, V.F.; Jin, S. Strongly nonlinear waves in 3D phononic crystals, APS—Shock Compression of Condensed Matter, AIP Conference Proceedings, Portland (OR), pp. 197-200 (2003).

Daraio, C.; Nesterenko, V.F.; Herbold, E.; Jin, S. Energy Trapping and Shock Disintegration in a Composite Granular Medium, Phys. Rev. Lett.; 96, 058002, (2006).

Daraio, C. and Nesterenko, V.F. Propogation of highly nonlinear signals in a two dimensional network of granular chains, 1419-1422, Amer. Institute of Physics, (2007).

Daraio, C.; Nesterenko, V.F.; Herbold, E.; Jin, S.Strongly nonlinear waves in a chain of Teflon beads. Physical Review E 72, 016603 (2005).

Daraio, C.; Nesterenko, V.F. Strongly nonlinear waves in a chain of polymer coated beads. Physical Review E; 73, 026612, (2006).

Daraio, C.; Nesterenko, V.F.; Herbold, E.; Jin, S. "Strongly nonlinear waves in polymer based phononic crystals". APS—Shock Compression of Condensed Matter, 1507-1510, AIP Conference Proceedings, Baltimore (MD), (2006).

Daraio, C.; Nesterenko, V.F.; Herbold, E.; Jin, S. Tunability of solitary wave properties in one dimensional strongly nonlinear phononic crystals, Phys. Rev. E; 73, 026610. (2006).

Dash, P.C., and Patnaik, K. Solitons in nonlinear diatomic lattices. Progress in Theoretical Physics, 65, pp. 526-541, (1981).

Doney, R. and Sen, S. Decorated, Tapered, and Highly Nonlinear Granular Chain, Phys. Rev. Lett. 97, 155502, (2006).

Doney, R. and S. Sen, Impulse absorption by tapered horizontal alignments of elastic spheres, 041304, Phys. Rev. E 72, (2005).

Goddard, J.D. Nonlinear Elasticity and Pressure-Dependent Wave Speeds in Granular Media, Proc. R. Soc. Lond. A 430, 105, (1990).

Goldenberg, C. and Goldhirsch, I. Friction enhances elasticity in granular solids, Nature, 435, 188-191, (2005).

Hascoët, E. and Herrmann, H.J. Shocks in Non-loaded bead chains with impurities. Eur. Phys. J. B 14, 183-190, (2000).

Herbold, E.B.; Nesterenko, V.F.; Daraio, C. Influence of Controlled Viscous Dissipation on the Propagation of Strongly Nonlinear Waves in Stainless Steel Based Phononic Crystals. APS—SCCM, 1523-1526, AIP Conference Proceedings, Baltimore (MD), (2006).

Herbold, E.B. Shock wave structure in a strongly nonlinear lattice with viscous dissipation, Phys. Rev. D 75, 021304 (2007).

Herbold E.B., Nesterenko V.F., Solitary and shock waves in discrete strongly nonlinear double power-law materials, Applied Physics Letters, 90, 261902, (2007).

Hinch E. J. and Saint-Jean, S. The fragmentation of a line of balls by an impact, Proc. R. Soc. A 455, 3201, (1999).

Hong, J. & Xu, A. Nondestructive identification of impurities in granular medium. Appl. Phys. Lett., 81, 4868-4870, (2002).

Hong, J. Universal power-law decay of the impulse energy in granular protectors. Phys. Rev. Lett. 94, 108001, (2005).

Hostler, S.R., Brennen, C E. Pressure wave propagation in a granular bed, Physical Review E, 72, 3, 031303, (2005).

Korteweg, D.J., and de Vries, G. On the change of form of long waves advancing in a rectangular canal, and on a New type of long stationary Waves. London, Edinburgh and Dublin Philosophical Magazine and Journal of Science, ser. 5, 39, pp. 422-443, (1895).

Lambert, R. F. and Tesar, J.S. Acoustic structure and propagation in highly porous, layered, fibrous materials. Journal of the Acoustical Society of America, 76, 1231-1237, (1984).

Lazaridi, A.N. and V.F. Nesterenko, Observation of new type of solitary waves in a one-dimensional granular medium, J. Appl. Mech. Tech. Phys. 26, pp. 405-408, (1985).

Manciu, F.S., Sen, S. Secondary solitary wave formation in systems with generalized Hertz interactions. Physical Review E 66, 016616. (2002).

Melo F, Job S, Santibanez F, et al. Experimental evidence of shock mitigation in a Hertzian tapered chain, Physical Review E 73, 4, 041305. (2006).

Nakagawa, M. et al. Impulse dispersion in a tapered granular chain Gran. Matt. 4, pp. 167-174, (2003).

Nesterenko, V. F., Daraio, C., Herbold, E. B. and Jin, S. Anomalous wave reflection at the interface of two strongly nonlinear granular media. Physical Review Letters 95, 158702, (2005).

Nesterenko, V.F., Propagation of nonlinear compression pulses in granular media, J. Appl. Mech. Tech. Phys. 5, pp. 733-743, (1984).

Rosas, A., Romero, A.H., Nesterenko, V.F., Lindenberg, K. Observation of Two-Wave Structure in Strongly Nonlinear Dissipative Granular Chains. Physical Review Letters, 98, 164301, (2007).

Rosas, A. and Lindenberg, K. Pulse velocity in a granular chain. Phys. Rev. E 69, 037601, (2004).

Rosenau P. and Hyman J.M. Compactions: Solitons with Finite Wavelength, Phys. Rev. vol. 70, No. 5, 564-567, (1993).

Sansalone, M. and Streett W. B. Impact-Echo Nondestructive Evaluation Concrete and Masonry, Bullbrier Press, ISBN: 0-96-12610-6-4, (1997).

Sen, S., Manciu, M., & Manciu, F.S. Ejection of ferrofluid grains using nonlinear acoustic impulses. Appl. Phys. Lett., 75, 10, 1479-1481, (1999).

Sen et al. Impulse Backscattering Based Detection and Imaging of Buried Objects in Granular Beds, SPIE 4394, 607, (2001).

Sen, S. and Manciu, M. Solitary wave dynamics in generalized Hertz chains: An improved solution of the equation of motion, Physical Review E, 64, pp. 056605, (2001).

Sen, S., Manciu, M., Wright J.D. Solitonlike pulses in perturbed and driven Hertzian chains and their possible applications in detecting buried impurities. Phys. Rev. E, 57, 2, 2386-2397, (1998).

Sen et al. Using mechanical energy as a probe for the detection and imaging of shallow buried inclusions in dry granular beds, Intl Journal of Modern Physics B, vol. 19, 2951-2973, (2005).

Sinkovits, R.S. and S. Sen, Nonlinear dynamics in granular columns, Phys. Rev. Lett. 74, pp. 2686-2689, (1995).

Sokolow A, Bittle EG, Sen, S. Solitary wave train formation in Hertzian chains, European Physics Letters, 77, 2, 24002, (2007).

Somfai E, Roux JN, Snoeijer JH, et al. Elastic wave propagation in confined granular systems Physical Review E 72, 2, 021301, (2005).

Vergara, L. Scattering of Solitary Waves from Interfaces in Granular Media. Phys. Rev. Lett. 95, 108002, (2005).

Jinying Zhu et al Imaging concrete structure using air-coupled impact-echo, J. Engineering Mechanics, 628-640, (Jun. 2007).

Carino, N. J. "Stress Wave Propagation methods," Chapter 14 of Malhotra, V.M. and Carino N. J. "Handbook on nondestructive testing of concrete CRC Press" (1991).

Job, S., Melo, F. Sen, S. & Sokolow, A. "How Hertzian solitary waves interact with boundaries in a 1D granular medium," Phys. Rev. Lett., 94, 178002, (2005).

Hertz, H. Journal fur Die Reine and Angewandie Mathematic, 92, pp. 156-171 (1881).

Gilles, B. and Coste, C. "Nonlinear elasticity of a 2D regular array of beads," Powders and Grains, Proceedings of the Fourth International Conference on Micromechanics of Granular Media, Sendai, May 21-25 (2001).

Herbold, E.B. Pulse propagation in a linear and nonlinear diatomic periodic chain, Acta Mech, 1-19, (Dec. 2008).

Herbold, E.B.; Kim, J.; Nesterenko, V.F.; Wang, S. Daraio, C.; "Tunable frequency band-gap and pulse propagation in a strongly nonlinear a diatomic chain", (Jun. 2008).

Porter, M.A., et al, Highly Nonlinear Solitary Waves in Heterogeneous periodic granular media, Physica D, 666-676, (Jan. 2009).

Porter, M.A.; Daraio, C.; Herbold, E.B.; Szelengowicz, I.; Kevrekidis, P.G. "Highly nonlinear solitary waves in periodic dimer granular chains" Physical Review E, 77, 015601(R), (Jan. 2008).

Nesterenko, V.F., Daraio, C., Herbold, E.B., Jin, S., Anomalous wave reflection at the interface of two strongly nonlinear granular media, The American Physical Society, Physical Review Letters PRL 95, 158702 (Published electronically Oct. 6, 2005).

Porter, M.A., Daraio, C., Herbold, E.B., Szelengowicz, I., Kevrekidis, P.G., Highly nonlinear solitary waves in periodic dimer granular chains, The American Physical Society, Physical Review E 77, 015601 (Published electronically Jan. 28, 2008).

PCT International Search Report for PCT/US2009/032958 filed on Feb. 3, 2009 in the name of California Institute of Technology and Chiara Daraio, et al.

PCT Written Opinion for PCT/US2009/032958 filed on Feb. 3, 2009 in the name of California Institute of Technology and Chiara Daraio, et al.

* cited by examiner

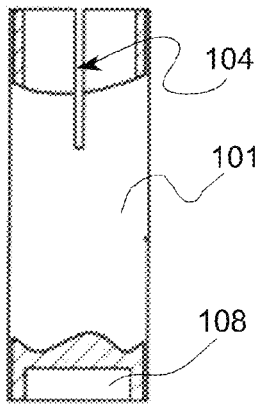
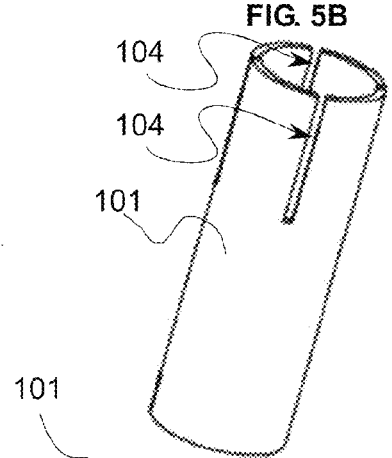
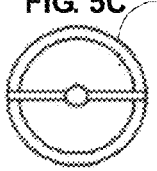
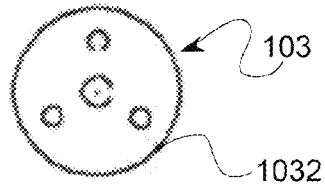
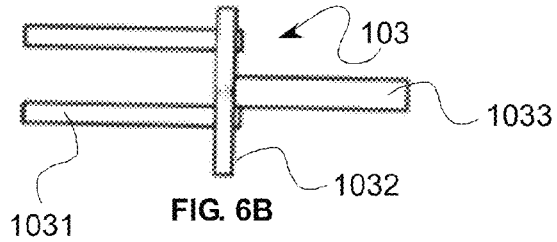
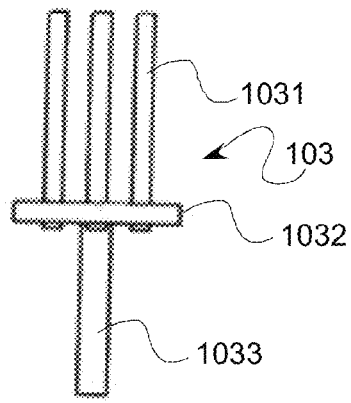
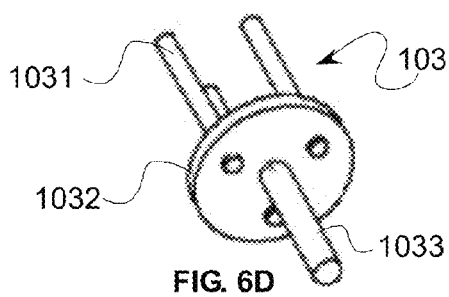

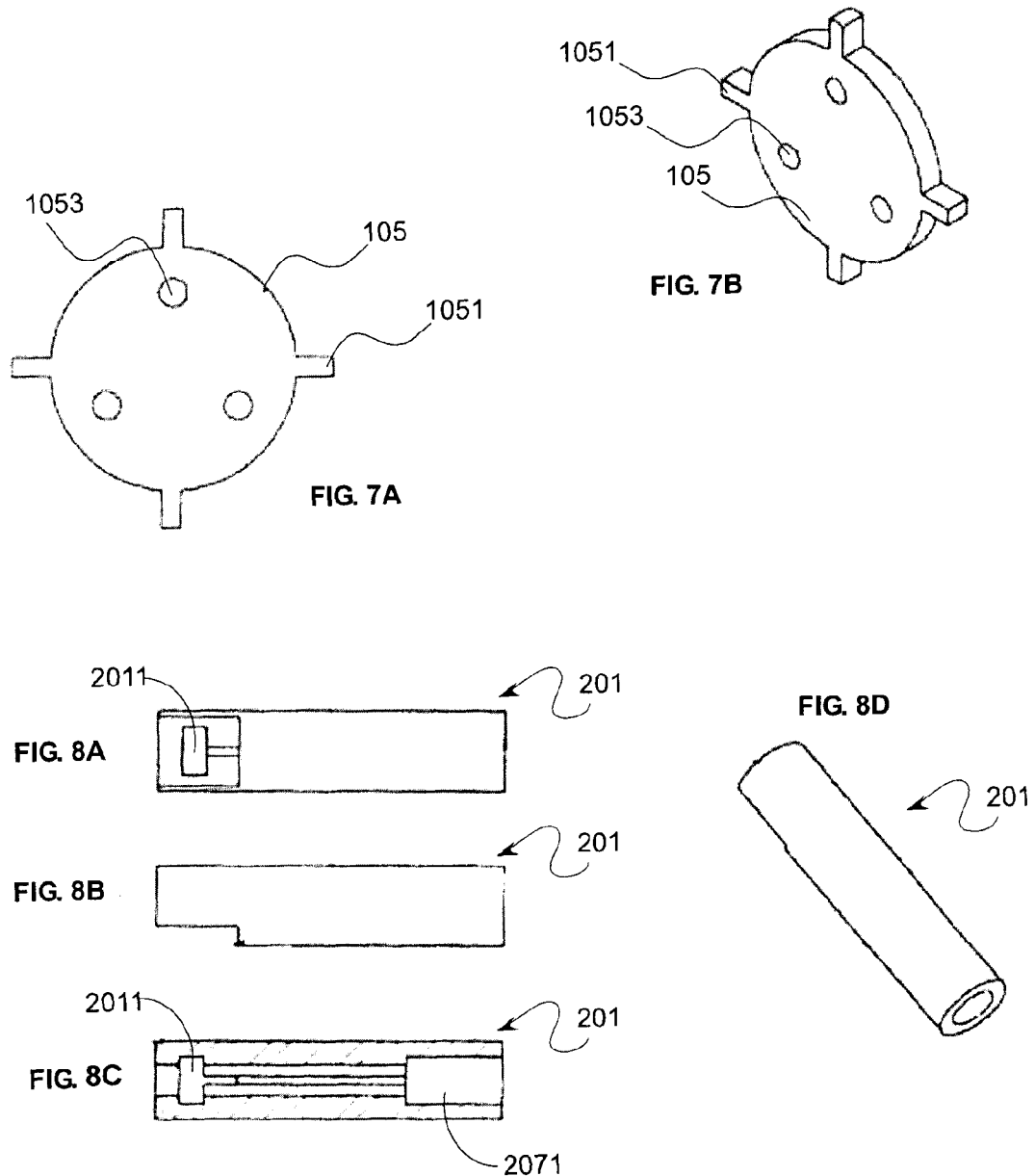

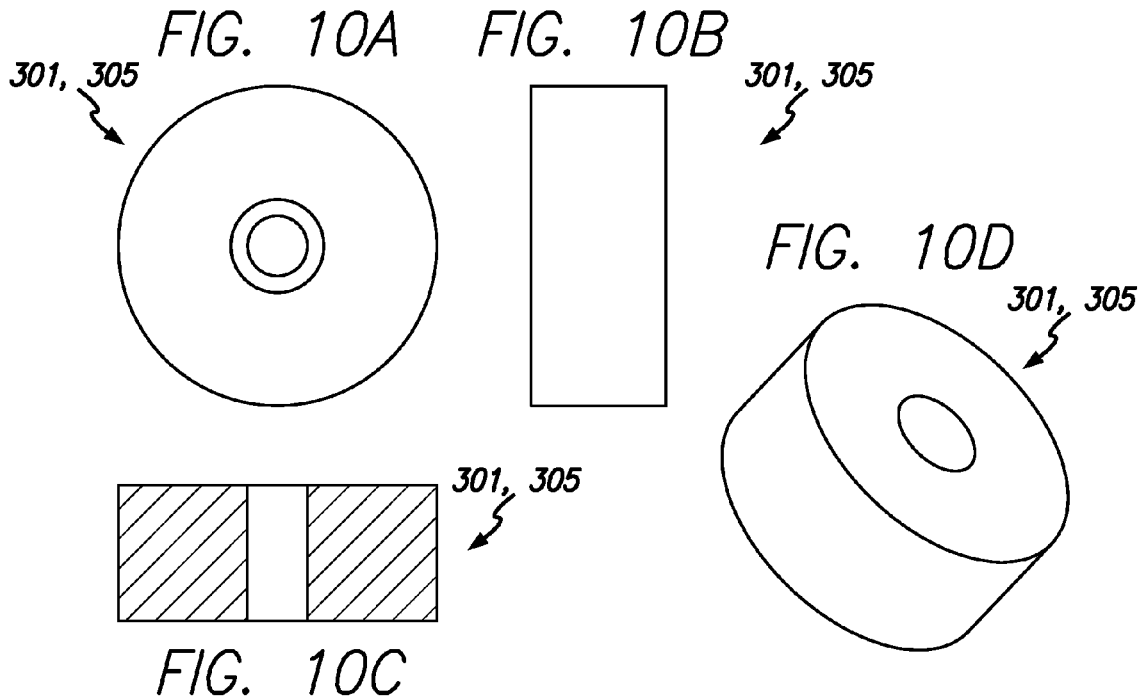
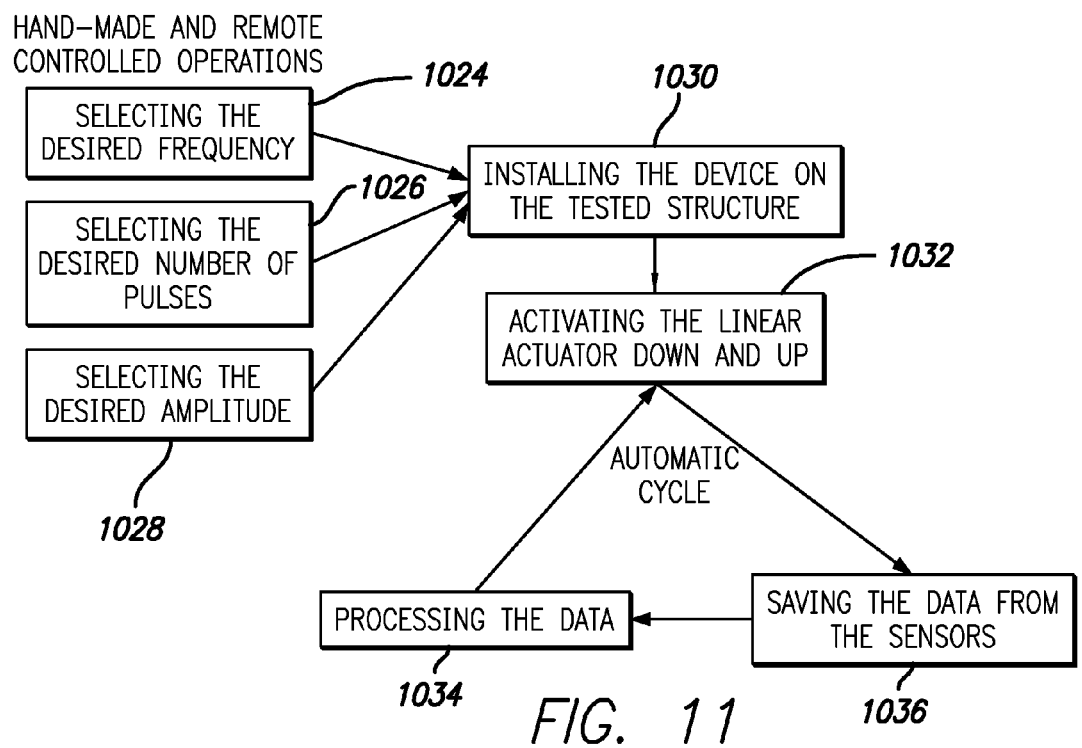

ACTUATION SYSTEM

CROSS-REFERENCE TO RELATED APPLICATIONS

The present application is related to and claims the benefit of the following copending and commonly assigned U.S. patent applications: U.S. Patent Application No. 61/063,903, titled "Method and device for actuating and sensing highly nonlinear solitary waves in surfaces, structures and materials," filed on Feb. 7, 2008; U.S. Patent Application No. 61/124,920, titled "Method and Apparatus for Nondestructive Evaluations and Structural Health Monitoring of Materials and Structures," filed on Apr. 21, 2008; U.S. Patent Application No. 61/135,266, "Automated Actuator Device for the Excitation of Tunable Highly Nonlinear Waves In Granular Systems," filed on Jul. 18, 2008; and U.S. patent application Ser. No. 12/251,164, "Method and Apparatus for Nondestructive Evaluation and Monitoring of Materials and Structures," filed on Oct. 14, 2008; where the entire contents of these applications are incorporated herein by reference.

BACKGROUND

1. Field

This disclosure relates to the excitation of highly nonlinear pulses with controlled desired pulse properties and transmitting them into a surface and/or detecting them from a surface. More particularly, the present disclosure relates to a method and apparatus for exciting controllable highly nonlinear pulses with desired shape, amplitude, frequency and duration to support nondestructive evaluation.

2. Description of Related Art

Non-destructive evaluation of a material or structure may be accomplished through the use of impact testing. In impact testing, the material or structure is typically struck with an impact device and sound waves propagating through the material or structure are then measured to provide some indication of defects within the material or structure. See, for example, U.S. Pat. No. 5,165,270 to Sansalone, et al., dated Nov. 24, 1992. In U.S. Pat. No. 5,165,270, the impact device is a number of differently weighted spheres that are each designed to produce a different duration of impact, thereby imparting different stress waves into the structure to be tested. The different stress waves have different frequency values depending on the impact duration. Each sphere is disposed on one end of a spring-steel rod. At the start of the test, a selected sphere is in a resting position. The sphere is withdrawn from the rest position by a pair of jaws to a given height above the structure. This action deflects the spring-steel rod, thus increasing the potential energy of the impact sphere. At a predetermined release point, the sphere is released causing it to impact the structure and impart a given energy to the structure. The impact produces stress (sound) waves that are reflected from the external surfaces and/or internal defects of the structure. The reflected waves are detected by a transducer that converts the normal surface displacements caused by the waves into an electrical signal. The electrical signal is then processed to provide an amplitude/frequency spectrum indicative of either the thickness of the structure or the defects disposed therein.

Other impact testing apparatus and techniques are known in the art, but generally use approaches similar to that described above, i.e., strike the material to be tested and measure the stress wave propagation. The impact devices (i.e., strikers) used in impact-testing technology typically cost several hundreds of dollars or more and need coupling to a signal conditioner. Line-powered signal conditioners are used to power sensors and condition their output signals for transmittal to readout and recording instruments. Impact hammers are used for delivering impulse forces into test specimens and the signal conditioner is used to provide electrical measurement signals of the amplitude and frequency content of the applied force. Hammers and conditioners used for non-destructive evaluation may be very expensive. Embodiments of the present invention as described below may provide for less costly apparatus for nondestructive evaluation of materials and structures.

SUMMARY

An embodiment of the present invention is a highly nonlinear wave actuating system that may be used for nondestructive evaluation (NDE) and/or Structural Health Monitoring (SHM) and/or quality control monitoring of structures and materials. The system has a spring loaded adjustable striker (that may be also replaced by an electronic piezo-actuator, a magnetically excited striker or a compressed air-based striker), a chain of particles and a trigger/loading device for the automated operation of the system. Through this combination of elements, the system may generate a single pulse or a train of distinct nonlinear pulses to be directed into a structure or material to be evaluated. The system may also include elements for the detection of intrinsic, formed or transmitted pulses (such as piezo sensors or magnetically sensed particle displacements) and wireless transmission (via, for example, a Bluetooth device) of data measured from the intrinsic, formed or transmitted pulses. The same system, when in passive mode (the striker in an off or non-operating position) may also be used as a sensor for the observation and detection of output waves (either intrinsic or externally excited) from the material/structure being tested. The system can be mounted on a holder to allow for point-contact unobtrusive operation, or adjacent to a planar surface as stand alone instrument. The actuator system may also be mounted in an array of such systems, to provide capabilities similar to that found in phase arrays or beam-forming arrays.

In another embodiment, the system comprises an actuator, formed by a spring loaded cylinder (that may be also replaced by an electronic piezo-actuator, a magnetically excited striker or a compressed air-based striker); a trigger; a cylindrical holder and a granular chain with embedded piezogauges or magnetically sensed particle displacements. In particular, the granular chain may consist of a one dimensional chain of granular components with adjustable diameters, including piezosensors for the detection of the traveling pulses. In this system, the properties of the signals can be tuned by the addition of static precompression (via, for example, a regulation screw), geometry variation and selection of appropriate materials for the fundamental components (grains). A receiving device is a system similar to the wave's exciter apparatus excluding the striker part.

BRIEF DESCRIPTION OF THE SEVERAL VIEWS OF THE DRAWINGS

FIGS. 5A-5D show various views of the striker body of the actuation system shown in FIGS. 3 and 4.

FIGS. 6A-6D show various views of the striker piston of the actuation system shown in FIGS. 3 and 4.

FIGS. 7A and 7B show various views of the cap of the actuation system shown in FIGS. 3 and 4.

FIGS. 8A-8D show various views of the dropper body of the actuation system shown in FIGS. 3 and 4.

FIGS. 10A-10D show various views of the particle chamber 301 of the actuation system shown in FIGS. 3 and 4.

FIG. 11 illustrates the different actions that may be taken to obtain data on the health of the structure facilitated by actuation systems such as those depicted in FIGS. 1-4.

DETAILED DESCRIPTION

Figure 1:
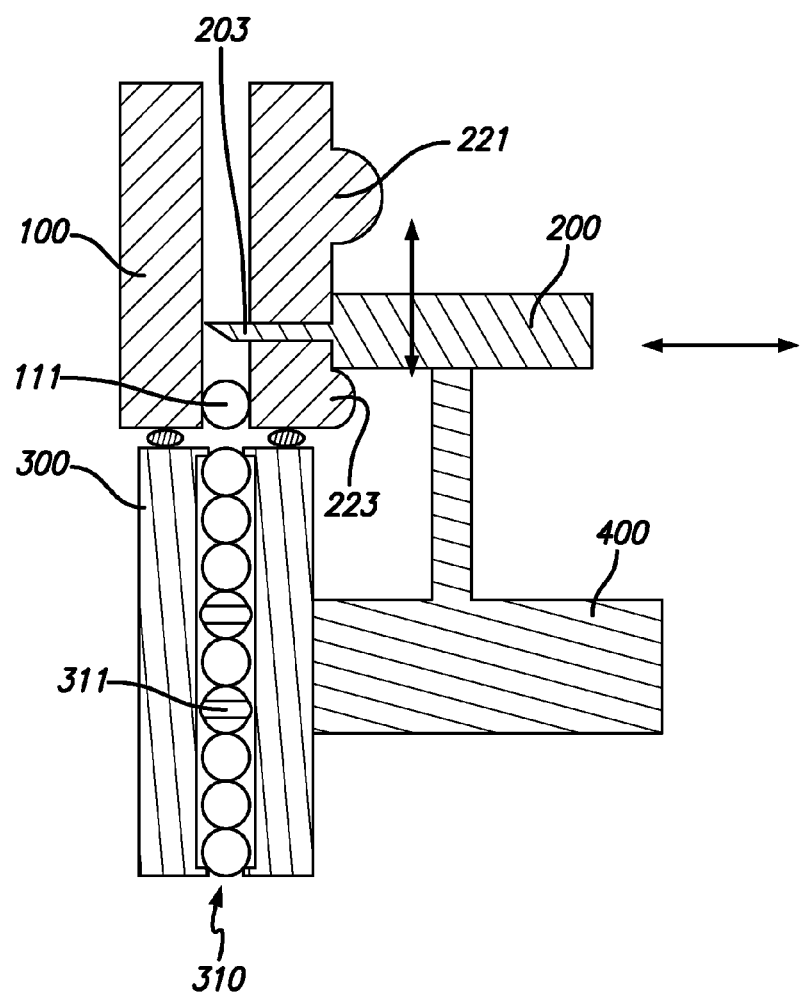
FIG. 1 shows a schematic of an actuation system.

Embodiments of the present invention may provide for nondestructive evaluation (NDE) and/or Structural Health Monitoring (SHM), and/or quality control monitoring of materials and structures through the use of highly nonlinear pulses and waves generated in one dimensional chains of granular components. In this disclosure, the granular components or grains may comprise granular matter, which is defined as an aggregate of particles or layers in elastic contact with each other, preferably in linear or network shaped arrangements. While the disclosure below describes the use of highly nonlinear pulses and waves, additional advantages may be provided when highly nonlinear solitary waves or pulses are used, generated, and/or detected. For purposes of this disclosure, highly nonlinear solitary waves are to be considered as a specific case of highly nonlinear waves. Additionally, highly nonlinear solitary pulses are to be considered as a specific case of highly nonlinear pulses. Hence, any references to highly nonlinear waves herein are to be considered as including highly nonlinear solitary waves and any references to highly nonlinear pulses herein are to be considered as including highly nonlinear solitary pulses unless otherwise denoted.

The contact interaction between the grains is regulated by the highly nonlinear force F—displacement δ relationship shown in Eq. 1:

$$F \approx A\delta^n \qquad \text{(Eq. 1)}$$

where A is a material's parameter and n is the nonlinear exponent (with n>1). An unusual feature of the granular state is the negligible linear range of the interaction forces between neighboring particles resulting in zero sound speed in an uncompressed material. This makes the linear and weakly nonlinear continuum approaches based on Korteveg-de Vries (KdV) equation invalid and places granular materials in a special class according to their wave dynamics. The dynamic response of granular materials is controlled by the highly nonlinear wave theory that supports the formation and propagation of highly nonlinear compact solitary waves.

In granular materials composed by perfectly spherical beads, the highly nonlinear behavior stems from the dynamics of the contact interactions, regulated by Hertz law, for which the exponent n in Eq. 1 is equal to 1.5. This highly nonlinear response can also be found in many other nonlinear systems composed by grains with different geometries and the theoretical formulation has been extended and generalized to all nonlinear exponents n, with n≠1. For example, other geometries may include irregular grains with conical contacts where n=2; forests of vertically aligned carbon nanotubes where n=2.2; transverse vibration in a fiber with discrete particles where n=3 and plug chain gas-liquid systems where n=3. The continuum treatment of the highly nonlinear wave theory extends to periodic heterogeneous media, such as, granular systems where the particles composing the chain are not identical, and periodic defects alternate throughout its length.

Highly nonlinear solitary waves are stationary pulses forming in ordered granular media by the balancing effects of their geometric nonlinearity and the dispersion present in the medium. A unique feature of the highly nonlinear solitary waves (that makes them different from all other previous solitary waves or solitons described in various other physical systems, such as in fluids, atomistics and electromagnetic waves), is the independence of their wave width from their amplitude. For granular systems, in which Hertz law is valid and the exponent n=1.5, their spatial size is always about 5 particles diameter, no matter what wave amplitude or wave speed is present in the system. Using the notation found in the most general treatment of the nonlinear wave theory, the wave equation for a uniform highly nonlinear system, derived from the Hertzian interaction law, is shown in Eq. 2 below:

$$u_{\tau\tau} = u_x^{n-1} u_{xx} + G u_x^{n-3} u_{xx}^3 + H u_x^{n-2} u_{xx} u_{xxx} + I u_x^{n-1} u_{xxxx} \qquad \text{Eq. 2}$$

where u is the displacement, τ is a rescaled time, n is the nonlinear exponent found in Eq. 1 and the explicit expression of the parameters I, H, G can be found in Porter, M. A.; Daraio, C.; Herbold, E. B.; Szelengowicz, I.; Kevrekidis, P. G. "Highly nonlinear solitary waves in phononic crystal dimers" Physical Review E, 77, 015601(R), 2008.

The solution for Eq. 2, describing the shape and properties of the highly nonlinear solitary waves, from direct integration is of the form shown in Eq. 3 below:

$$u_\xi = v = B\cos^{\frac{2}{n-1}}(\beta\xi), \qquad \text{Eq. 3}$$

where $$B = \left(\frac{\mu}{[\beta^2 s(s-1)]}\right)^{\frac{1}{n-1}}, \beta = \sqrt{\sigma}\frac{(1-\eta)}{2} \text{ and } s = pl.$$

The generality of the highly nonlinear wave equation shown in Eq. 2 is given by the fact that it includes also the linear and weakly nonlinear regimes of wave propagation. These regimes can be extrapolated by adding an initial prestrain (precompression) to the system. Its solution demonstrates that in a highly nonlinear medium only two harmonics contribute to a stationary mode of propagation of the periodic signal. The solitary shape, if the initial prestrain $\xi_0$ is approaching 0, can be taken as one hump of the periodic solution provided by Eq. 3 with finite wave length equal only to five particle diameters in the case of a Hertzian granular system. In analogy with the KdV solitons, the highly nonlinear solitary waves are supersonic, which means that their phase velocity is larger than the initial sound velocity ($c_0$) in the nonlinear medium (especially in the case of an uncompressed system, in which the $c_0$=0). For granular chains composed by spherical particles, the speed of the solitary wave $V_s$ as nonlinear function of the maximum particle dynamic strain can be expressed as shown in Eq. 4:

$$v_s = \frac{2}{\sqrt{5}} c \xi_m^{\frac{1}{4}} = 0.6802 \left( \frac{2E}{a \rho^{\frac{3}{2}}(1-v^2)} \right)^{\frac{1}{3}} F_m^{\frac{1}{6}}, \quad \text{Eq. 4}$$

where $F_m$ is the maximum dynamic contacts force between the particles in the discrete chain.

The relationship shown in Eq. 4 may provide for applications in the field of dynamics and acoustic properties of materials. Such waves, as predicted by the theory and validated numerically and experimentally, have tunability characteristics. By changing the mechanical and/or the geometrical properties of the high nonlinear medium supporting the formation of HNWs, the shape and the properties of the traveling pulse can be tuned. In other words, the properties of the nonlinear waves in the highly nonlinear media can be "engineered" for a specific application. These "controllable" waves may then be used as new boundary conditions in various structures for testing. It may also be desirable to generate a train of nonlinear waves rather than a single nonlinear pulse.

The analytical expression for the tunability of the solitary waves speed in a Hertzian system derived from the presence of added precompression and obtained from the discretization of the particles in the chain, is expressed as shown in Eq. 5 below:

$$v_s = 0.9314 \left( \frac{4E^2 F_0}{a^2 \rho^3 (1-v^2)^2} \right)^{\frac{1}{6}} \frac{1}{\left( f_r^{\frac{2}{3}} - 1 \right)} \left\{ \frac{4}{15} \left[ 3 + 2 f_r^{\frac{5}{3}} - 5 f_r^{\frac{2}{3}} \right] \right\}^{\frac{1}{2}}. \quad \text{Eq. 5}$$

where $F_0$ represents the static prestress (precompression) added to the system, $f_r = F_m/F_0$ and $F_m$ is the maximum contacts force between the particles in the discrete chain.

The dependence of the solitary wave properties on the materials parameters is shown in Eq. 4 for a non-prestressed system and in Eq. 5 for a prestressed system. Also note that, with HNSWs, the system is size independent but sensitive to the presence of periodic heterogeneities in the chain. Therefore, the solitary waves may be scalable to various sizes, according to the needs of each specific application.

According to Eqs. 4 and 5, the tunability of the HNSWs can be achieved by varying one or more parameters of the nonlinear medium. For example, increasing the particle size of the highly nonlinear medium increases the wavelength and the wave speed and amplitude decrease. This tunability provides the possibility of reducing or eliminating the electronic equipment, such as function generators, necessary to excite stress waves of a given shape and wavelength. Therefore, the use of HNWs may reduce some of the power demands in ultrasonic actuation needed by prior art systems and may allow the use wireless technology instead of tethered technology known in the art. In addition, the high-sensitivity of wave amplitude and wave speed to the state of stress state in highly nonlinear material may also allow for improvements in the estimation of applied stress over that obtained by conventional acoustoelastic methods.

Particles having morphology different than the one described by the classical Hertzian shape (n=1.5) may be used, which can add another element to the tunability, that is by varying n in Eq. 1 the wavelength (and, therefore, the signal's frequency) will vary significantly. Further, a HNW or HNSW traveling in a system composed of alternating short chains of hard and soft beads (that can be interpreted as defects) or in any periodic heterogeneous system will induce significant changes in the properties of the traveling pulse. Systems composed of randomized assemblies of particles, such as chains including particles of different materials, masses and diameters in a disordered and quasi-disordered configuration, present thermalization phenomena that induce pulse decomposition and excitation of higher frequency modes.

The use of solitary waves for defect and impurity detection in granular media is discussed in Sen, S., Manciu, M., and Wright, J. D., "Solitonlike Pulses in Perturbed and Driven Hertzian Chains and Their Possible Applications in Detecting Buried Impurities," Phys. Rev. E, 57, no. 2, 2386-2397 (1998) and in Hong, J. & Xu, A., "Nondestructive identification of impurities in granular medium." Appl. Phys. Lett., 81, 4868-4870 (2002). Solitary waves have been demonstrated to be sensitive to the granular materials properties, such as elastic modules, and applied stress and the dependence of the velocity and shape of the backscattered signal on the presence of light and heavy impurities in a granular chain have also been noted. Highly nonlinear solitary pulses have been studied numerically and experimentally in various one-dimensional highly nonlinear systems assembled from chains of stainless-steel, glass, brass, nylon, polytetrafluoroethylene (PTFE) and Parylene coated steel beads. As predicted by the theoretical formulation, the numerical and experimental validation showed a significant difference in the speed and amplitude of the supported solitary waves as a function of the materials parameters.

In an embodiment according to the present invention, a chain of beads, held in place in the holder, is in contact with a structure to be tested, and can be pre-compressed by two extremity caps. A striker device is composed of a dropping apparatus, a propelling apparatus and a reloading apparatus, as well as at least one striker bead, which can be a bead similar to the ones in the chain of beads, or a cylindrical bead, from the same diameter but of a different mass. The reloading apparatus may be a linear actuator that goes up and down. The action of the reloading apparatus may be under the control of a wireless device. When the linear actuator is in an upper position, a camshaft system (or other system) allows the dropping apparatus to drop the striker bead. The striker bead will then drop to strike the chain of beads. At the end of dropping, the reloading apparatus goes back to its lower position, which allows the dropping apparatus to engage the bead back, and a new cycle may repeat.

The force at which the striker bead strikes the chain of beads may be increased by using a spring that contacts a piston disposed above the striker bead and within the propelling apparatus. As the dropping apparatus disengages in the upper position, a loaded spring releases, causing both a piston disposed above the striker bead and the striker bead to gain momentum. The travel of the piston may be limited by a stopper part, so that the striker bead flies freely before hitting the chain of beads. A ring, which may screwable on a body of the propelling apparatus, may be used to adjust the pre-compression of the spring that contacts the piston. The precompression may also be performed with a second linear actuator, and commanded by the same wireless technology as the reloading apparatus. A damping device may also be used between the propelling apparatus and the holder of the chain of beads, to reduce the noise due to the hit of the piston on the stopper part.

An embodiment according to the present invention is a system comprising an actuator, formed by a spring loaded cylinder, a trigger, a cylindrical holder and a granular chains with embedded piezogauges. This embodiment may be used to generate a HNW. In one embodiment, the granular chain consists of a one dimensional chain of granular components with adjustable diameters, including piezosensors for the detection of traveling pulses. In this embodiment, the properties of the signals can be tuned by the addition of static precompression (screw regulated), geometry variation and selection of appropriate materials for the fundamental components. Another embodiment is a receiving device that is a system similar to the HNW generator embodiment excluding the striker part.

FIG. 1 shows a schematic of an actuation system according to the present invention. In FIG. 1, a particle chain camber 300 contains a chain of particles 310 to be used to generate highly nonlinear waves. The chain of particles 310 may have one or more piezosensing particles 311 that may be used to detect highly nonlinear waves propagating through the chain of particles 310. Alternatively, instead of or in addition to the piezo-sensing particles, apparatus for magnetically sensing particle displacements may be used to detect the highly nonlinear waves, or other such force sensing apparatus may be used. Further, the piezo-sensing particles, magnetic apparatus, or other such force sensing apparatus may be coupled to transmission devices to transmit measured data to data collection devices. Such transmission devices could, therefore, provide for a remote monitoring capability. Further, such transmission devices could be directly wired to data collection devices or employ wireless transmission techniques, such as radio frequency or infrared technologies, to transmit data to data collection devices.

The bottom end of the chamber 300 can be placed against a structure to be tested. A striker structure 100 contains at least one striker particle 111. A dropper structure 200 has a dropper pin 203 that moves horizontally to engage and release the striker particle 111, as described in additional detail below. The horizontal motion of the dropper structure 200 is facilitated by an upper cam 221 and a lower can 223. A linear actuator structure 400 is used to move the dropper structure 200 vertically to allow the dropper structure 200 to lift the striker particle 111 to some height above the chain of particles 310. Release of the striker particle 111 occurs when the dropper structure travels over the upper cam 221 located near the top of the striker structure 100. The linear actuator structure 400 will then move the dropper structure 200 near the bottom of the striker structure 100 to allow the dropper pin 203 to extend beneath the striker particle 111 (by traveling over the lower cam 223) to allow the striker particle 111 to be lifted again. Note that the striker structure 100 shown in FIG. 1 appears to merely drop the striker particle 111. However, other embodiments may have an electro-piezo actuator, a magnetically excited striker, or a compressed air striker applying a force to the striker particle 111 to launch it towards the chain of particles. Further note that the application of such force may allow for the generation of single pulses or train of distinct pulses based on the type and duration of the initial impact or excitation.

Figure 2:
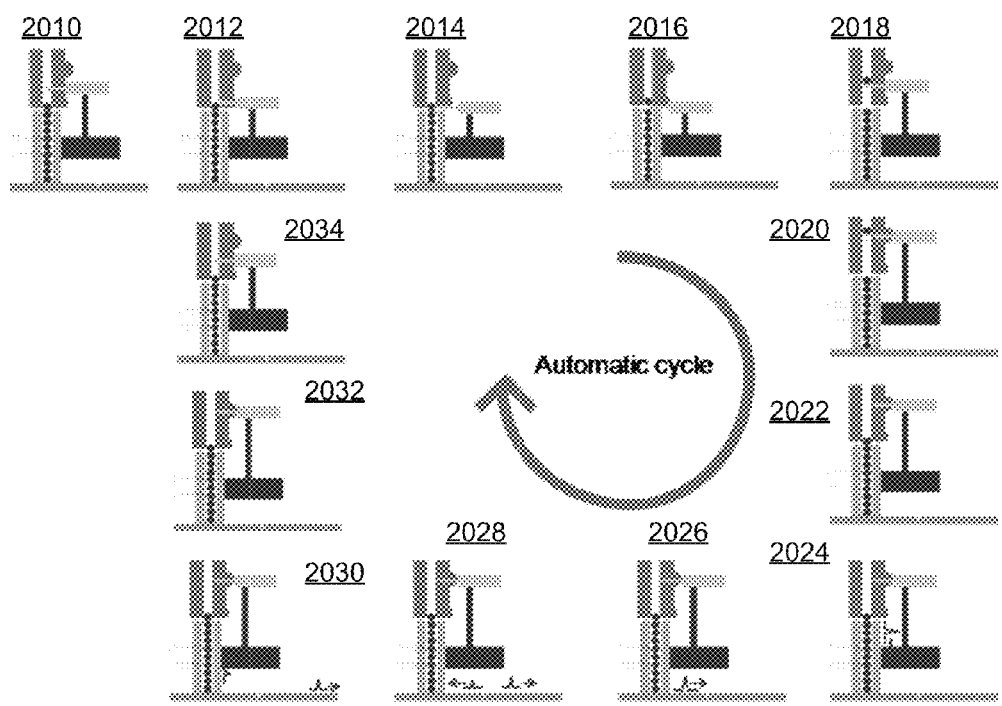
FIG. 2 shows a cycle of the actuation system shown in FIG. 1.

FIG. 2 shows a cycle of the embodiment depicted in FIG. 1. Step 2010 depicts a phase where the striker particle 111 rests on top of the chain of particles 310. Step 2012 depicts the dropper structure 200 traveling over the lower cam 223 causing the dropper pin 203 to retract slightly and slide over the striker particle 111. Step 2014 shows the dropper pin 203 sliding past the striker particle 111. Step 2016 shows the dropper pin 203 positioned beneath the striker particle 111. Step 2018 shows the dropper structure 200 moving upwards and the striker particle 111 being lifted by the dropper pin 203. Step 2020 shows the dropper structure moving over the upper cam 223, causing the dropper pin 203 to be retracted from beneath the striker particle 111. Step 2022 shows the striker particle 111 hitting the top particle in the chain of particles 310. Step 2024 shows the highly nonlinear pulse resulting from the striker particle 111 hitting the chain of particles 310 and propagating through the chain of particles 310. Note that the chain of particles may generate a train of distinct nonlinear pulses. Step 2026 shows the highly nonlinear pulse propagating through the structure under evaluation. Step 2028 shows a backward propagating pulse resulting from the generated nonlinear pulse traveling through a discontinuity in the structure to be evaluated. Step 2030 shows the backward propagating pulse traveling through the chain of particles 310 for detection by one or more piezo-sensing particles 311. Note that sensors other than the piezo-sensing particles 311 in the particle chain chamber 300 may be used to detect the backward propagating pulse. Step 2032 shows the system in preparation for the next cycle where step 2034 shows the dropper structure 200 being lowered to pick up the striker particle 111 again.

Figure 3:
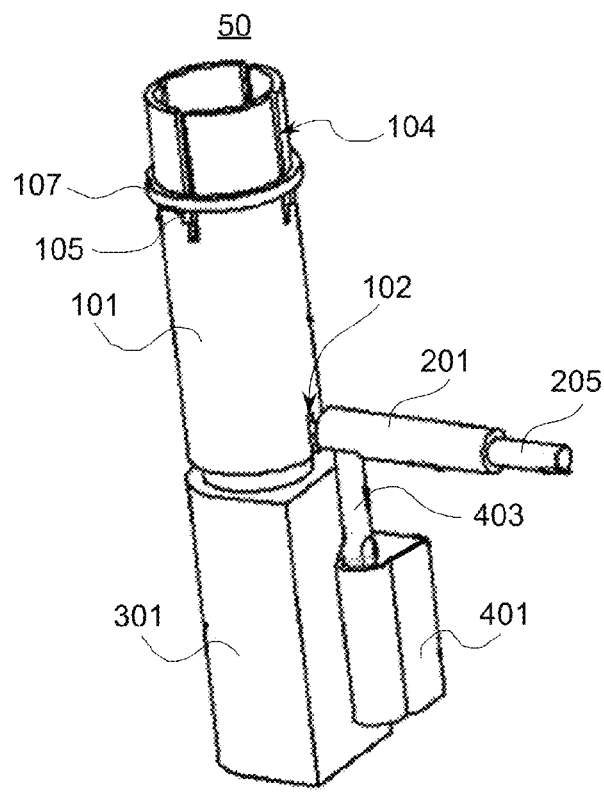
FIG. 3 shows an external view of another actuation system.
Figure 4:
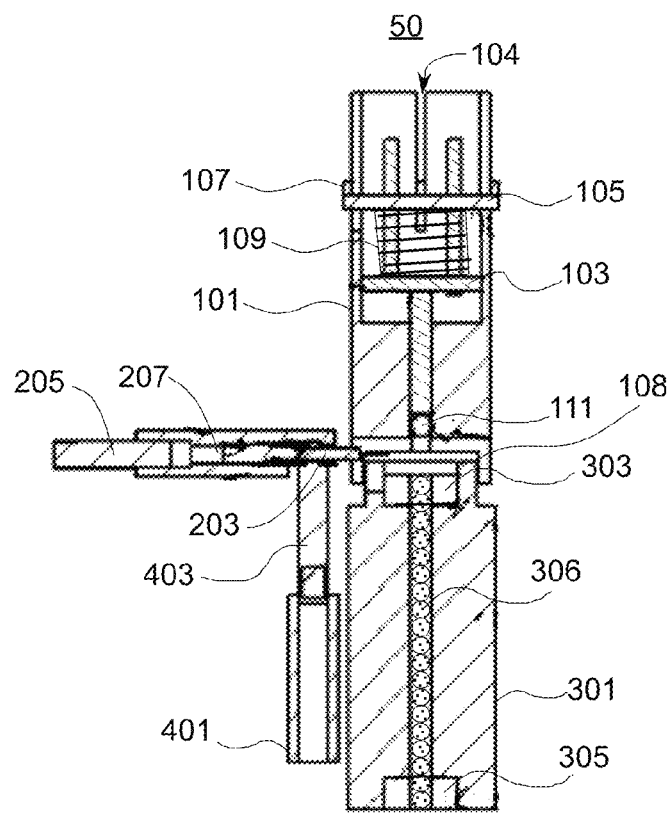
FIG. 4 shows a cut away view of the actuation system depicted in FIG. 3.

FIG. 3 shows an external view of another actuation system 50 according to the present invention and FIG. 4 shows a cut away view of that actuation system 50. In FIG. 3, a striker body 101 is disposed above a particle chamber 301. A linear actuator 401 is affixed to the side of the particle chamber 301, which moves a dropper body 201 up and down by means of an actuator piston 403. FIG. 4 shows the internal components of the actuator system 50. Inside the striker body is a striker piston 103 that moves up and down within the striker body 101. The striker piston 103 is disposed above the striker particle 111. Inside the dropper body 201 is a dropper pin spring 207 that contacts the dropper pin 203. A dropper spring 205 is used to adjust the tension force on the dropper pin 203. In a manner similar to that described above, the dropper pin 203 projects beneath the striker particle 111 and is then used to move the striker particle 111 vertically. The actuator piston 403 of the linear actuator 401 moves the dropper body 201 and the dropper pin 203. As the striker particle 111 moves vertically, the striker piston 103 immediately above the striker particle 111 will compress a cap spring 109 against a cap 107. The cap 107 is held in place by a nut 105 and cap slots 104 in the striker body 101. The nut 105 can be adjusted vertically to adjust the amount of force against the striker piston 103 when the striker piston 103 is moved to the release position. A portion of the particle chamber 301 fits within a striker body cavity 108. The particle chamber 301 contains a chain of particles 306 in linear contact with each other. Particle chamber caps 303, 305 are disposed at each end of the particle chamber 301 and may be used to apply some compress to the particles 306 within the chain.

FIGS. 5A-5D show various views of the striker body 101. FIG. 5A shows a partial cut-away view of the striker body and shows the cap slots 104 and the striker body cavity 108. FIG. 5B shows an isometric view of the striker body 101. FIG. 5C shows a top down view of the striker body 101. FIG. 5D shows a side view of the striker body 101 showing a cap slot 104 and a dropper pin slot 106 within which the dropper pin 203 moves.

FIGS. 6A-6D show various views of the striker piston 103. FIG. 6A shows a top down view of the striker piston 103 with a striker piston plate 1032. FIG. 6B shows a side view of the striker piston 103 showing a striker piston plunger 1033 disposed on one side of the striker piston plate 1032 and striker piston arms 1033 disposed on the other side of the striker piston plate 103. FIG. 6C shows another side view of the striker piston 103. FIG. 6D shows an isometric view of the striker piston 103.

FIGS. 7A and 7B show various views of the cap 105. FIG. 7A shows a top down view of the cap 105 and shows the striker piston arm holes 1053 through which the striker piston arms project. The combination of the striker piston arms 1033 and the striker piston arm holes 1053 provide stability to the striker piston 103 as to moves up and down within the striker body 105. FIG. 7A also shows the cap tabs 1051 that fit within the cap slots 104 within the striker body 101 to provide stability to the cap 105. FIG. 7B shows an isometric view of the cap 105.

Figure 9A:
FIGS. 9A-9C show various views of the dropper pin that fits within the dropper body depicted in FIGS. 8A-8D.
Figure 9B:
Figure 9C:
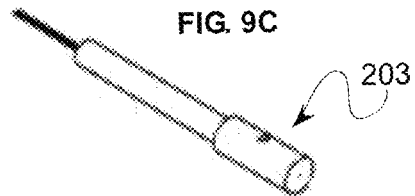

FIGS. 8A-8D show various views of the dropper body 201. FIG. 8A shows a bottom view of the dropper body 201 and dropper to actuator assembly 2011 within the body 201. The dropper body 201 connects to the actuator piston 403 at the dropper to actuator assembly 2011. FIG. 8B shows a side view of the dropper body 201. FIG. 8C shows a cut away bottom view of the dropper body 201 with dropper to actuator assembly 2011 and a dropper pin screw cavity 2071 within which the dropper pin screw 207 fits. FIG. 8D shows an isometric view of the dropper body 201. FIGS. 9A-9C show various views of the dropper pin that fits within the dropper body 201.

FIGS. 10A-10D show various views of the particle chamber 301. FIG. 10A shows a top view of the particle chamber 301. FIG. 10B shows a cut-away side view of the particle chamber 301. As shown in FIG. 10B, a particle area 3014 is within the center of the particle chamber 301. In operation, the chain of particles 306 is disposed within the particle area 3014. Cavities 3015, 3013 within the particle chamber 301 are provided to receive the particle chamber caps 303, 305. FIG. 10B also shows the particle chamber slot 3019 through which the dropper pin 203 travels. FIG. 10C shows a side view of the particle chamber 301 having a striker body coupler section 3017 that fits within the striker body cavity 108 when the particle chamber 301 is assembled to the striker body 101. FIG. 10D shows an isometric view of the particle chamber 301. FIGS. 10A-10D show various views of the particle chamber caps 303, 305.

The actuation system 50 depicted in FIGS. 3 and 4, and its components illustrated in FIGS. 5A through 10D operates similar to the system depicted in FIG. 1. The particle chamber 301 with the chain of beads 306 is disposed against a structure to be evaluated. The striker body 101 is assembled to the particle chamber 301. The dropper pin 203 projects beneath the striker particle 111 and is lifted by the actuator arm. As the striker particle 111 is lifted, the striker piston 103 causes the cap spring 109 to compress against the cap 107. The nut 105 is used to adjust the position of the cap 107 to provide a predetermined amount of force against the striker piston 103 and the striker particle 111 when the striker particle 111 is lifted to its release position. A cam (not shown) causes the dropper pin 203 to be extracted from beneath the striker particle 111 when the striker particle 111 reaches its release position. When released, the striker particle 111 is pushed by the striker piston 103 against the particle chamber 301. This will cause an impact pulse to travel through the chains of particles 306. The linear actuator 401 will then activate to move the dropper pin to the bottom of the striker body 201 and start the actuation process over. Sensors may be disposed within the chain of beads 306, the striker body 101, the dropper body 201, and/or the linear actuator 401 to allow for remote monitoring and control of the actuation system 50.

FIG. 11 illustrates the different actions that may be taken to obtain data on the health of the structure facilitated by embodiments of the present invention. Steps 1024, 1026, and 1028 show some of the parameters that may be selected to control the actuation system. As shown, selecting the desired frequency 1024 of the pulses, selecting the desired number of pulses 1026, and selecting the desired amplitude 1028 of the pulses may be performed prior to operating the actuation system. As indicated above, the amplitude of the pulses may be set by controlling the spring tension against the striker piston while the frequency and number of pulses may be controlled by the remote control of the actuation system. Note that steps 1024, 1026, and 1028 are preparatory actions that can either be done by hand or remotely. After the determination of the parameters to be used, the actuation system may be installed in the structure to be tested as shown in step 1030. After installation, the actuation system can be operated by activating the linear actuator, as shown in step 1032, and data collected from sensors, step 1036, and processed, step 1034.

Figure 12:
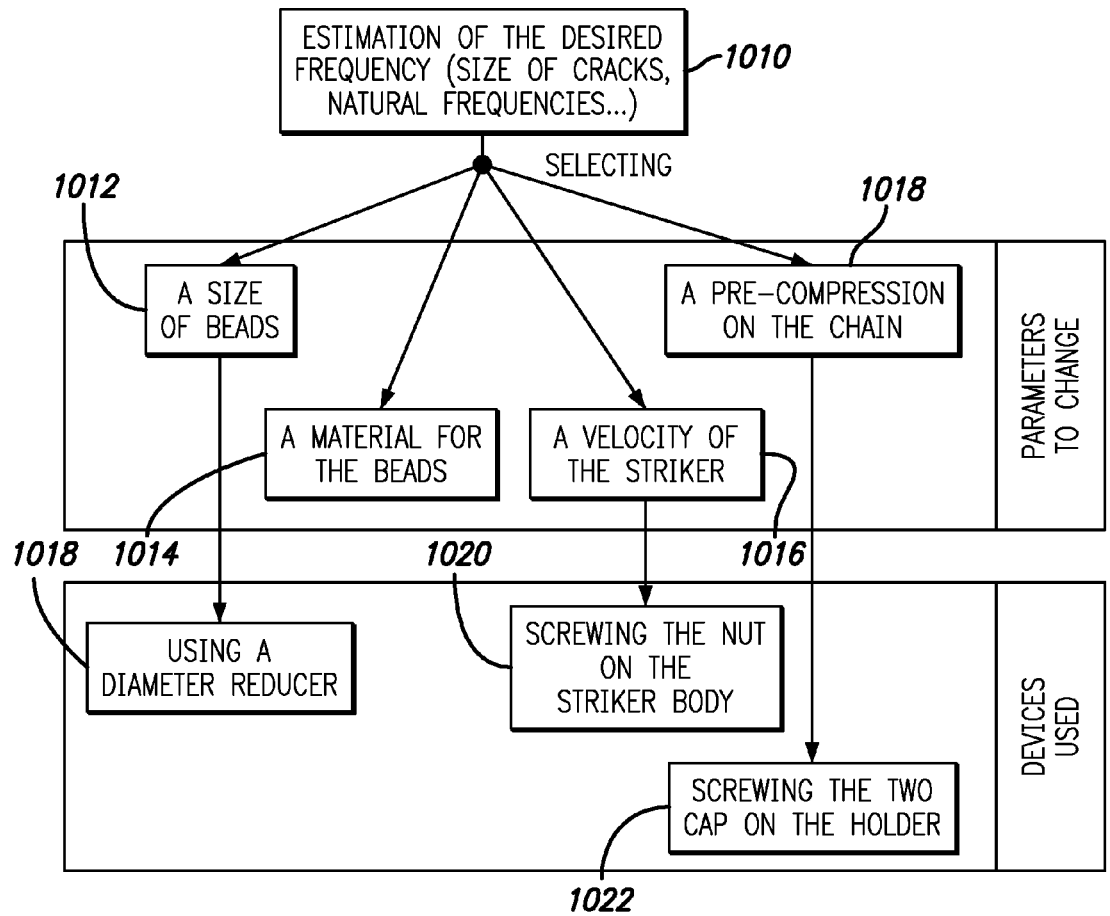
FIG. 12 summarizes the different parameters that can be tuned by various parts of actuation systems such as those depicted in FIGS. 1-4.
Figure 13:
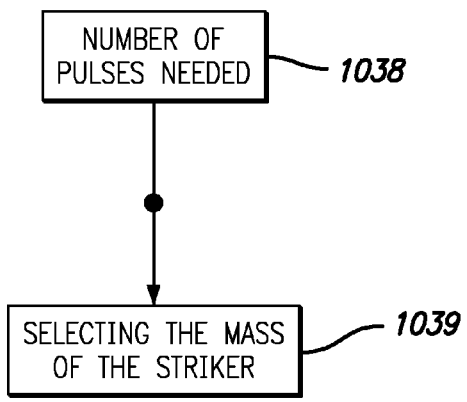
FIG. 13 shows another example of how a parameter of the actuation system can be selected.

FIG. 12 summarizes the different parameters that can be tuned by various parts of embodiments according to the present invention. As shown in step 1010, an estimate of the desired operation frequency of the actuation system may be performed based on the size of cracks within the structure to be evaluated, the natural frequencies of the structure, or other parameters. This information may then be used to select the size of particles used within the actuation system 50, step 1012; material for the particles, step 1014; precompression on the chain of particles, step 1018; or the velocity at which the striker particle moves, step 1016. As indicated in FIG. 12, the size of the particles may be adjusted by using a diameter reducer, step 1018, and see also the discussion below on the diameter reducer. As indicated in FIG. 12 and discussed above, the velocity of the striker can be adjusted by changing the position of the nut 105 on the striker body 101. As also indicated in FIG. 12 and discussed above, precompression of the chain of beads can be achieved by tightening or loosening the particle chamber caps 303, 305. FIG. 13 shows another example of how a parameter of the actuation system can be selected. As shown in FIG. 13, the number of desired pulses to be transmitted into the structure to be evaluated, step 1038, can be determined by selecting the mass of the striker particle, step 1039.

Figure 14:
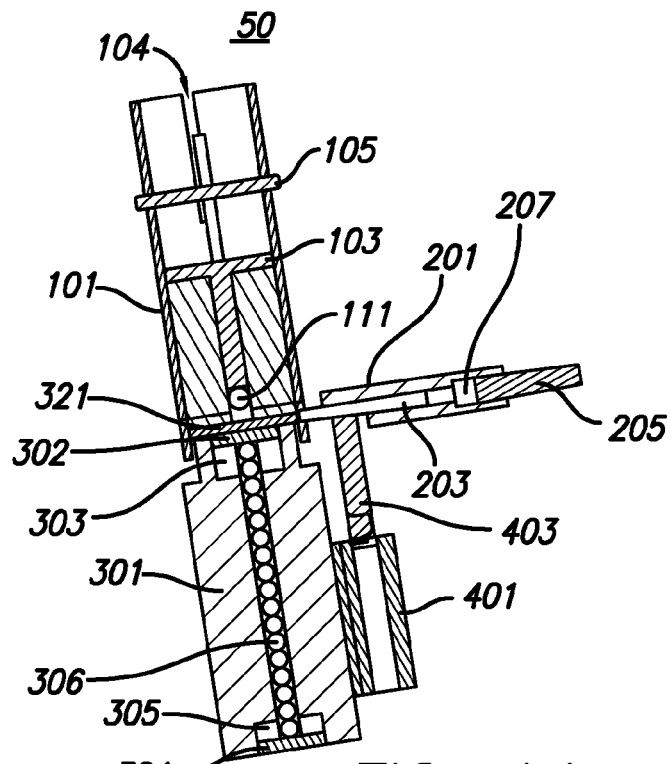
FIG. 14 shows a cut-away view of another actuation system.
Figure 15:
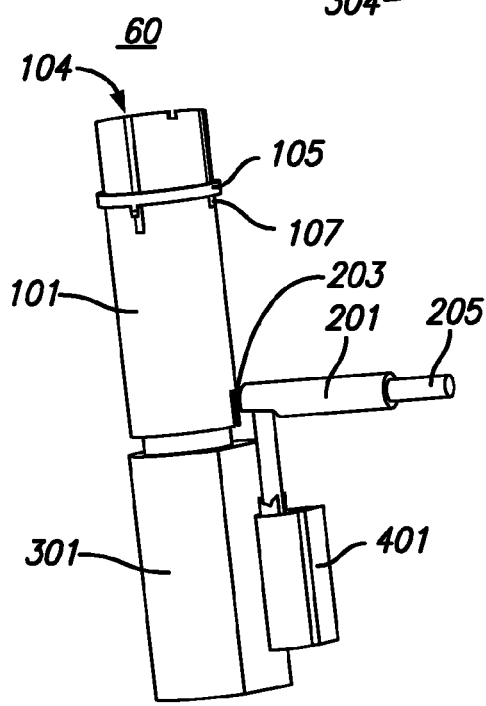
FIG. 15 shows a solid view of the actuation system depicted in FIG. 14.

FIGS. 14 and 15 illustrate another actuation system 60 according to am embodiment of the present invention similar to the actuation system 50 depicted in FIGS. 3 and 4. FIG. 14 shows a cut-away view, while FIG. 15 shows a solid view. The actuation system 60 shown in FIG. 14 has the striker body 101 is disposed above the particle chamber 301. The linear actuator 401 is affixed to the side of the particle chamber 301, which moves the dropper body 201 up and down by means of the actuator piston 403. Other components of the actuator system 60 are similar to those depicted in FIGS. 3 and 4. Like components are numbered the same. However, the actuator system shown 60 shown in FIG. 14 has a damping material 321 disposed between the striker body 101 and the particle chamber 301. This damping material 321 may limit any noise caused by the travel of the piston 103 within the striker body 101 within the system 60. The upper particle chamber cap 303 may have an upper cap layer 302 to receive the striking force from the striker particle 111. Similarly, the lower particle cap 305 may also have a lower cap layer 304 to transfer nonlinear waves generated within the chain of beads 306 into a structure under test.

Figure 16:
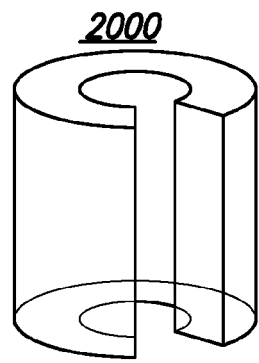
FIG. 16 depicts a diameter reducer that may be used to modify the operation of an actuator system.

FIG. 16 depicts a diameter reducer 2000 that may be used to modify the operation of an actuator system. The diameter reducer 2000 may be placed around different size beads within a chain of beads or around a striker particle 111. The diameter reducer 2000 therefore allows different sized beads to be used within an actuation system and thus modify the characteristics of nonlinear waves produced by the actuation system, as indicated in FIG. 12.

In an embodiment according to the present invention, an actuation system, such as one of those described above, may be placed on a structure to be tested. A user may select a desired frequency, by screwing a ring on the striker body 101 and the desired number of pulses, by selecting the mass of the striking bead, before launching the process. The striking bead, set in motion at a defined velocity will generate a pulse in the chain of particles 306. This pulse, its amplitude, its length, its shape will be detected by a sensor or sensors disposed within the chain of particles 306, on the particle chamber 301, or elsewhere, and the information can be transmitted by wireless technology. As the pulse propagates in large structures, every default, edge, and contact can send reflected pulses back to the chain of particles 306. The shape, time of arrival, amplitude and length of the reflected pulse can also be transmitted by wireless technology. Within smaller structures or parts, embodiments according to the present invention may be used to excite natural frequencies, which can also generate pulses back in the chain. By analyzing received data, a map of any tested structure may be generated.

In the description above, the use of a single actuation system to generate a non linear pulse or series of nonlinear pulses. However, in alternative embodiments, an actuation array or arrays may be configured from several actuation systems. Controlling the time or rate at which the several actuation systems generate pulses may allow an actuation array to create an actuation pulse beam that can be steered to propagate in a desired direction or directions. This would be similar to phased array systems or beam-forming arrays known for radio frequency based systems. Modifying the pulse characteristics as described above along with or instead of controlling the pulse rate or time may also allow an actuation array consisting of several actuation systems to generate steered pulse beams.

As indicated above, embodiments of the present invention may provide the capability to detect pulses reflected back from the material or structure into which pulses have been transmitted. These embodiments may also be configured to detect intrinsic noise, sound, waves or vibrations from a structure or material, that is, to detect vibrations that are not the result of pulses generated from the actuation system. Still other embodiments may be a "passive receiver" that do not have the striker structure described above and just simply detect intrinsic noise, sound, waves or vibration from a structure or material using a chain of granular particles, without the need of external excitations.

As indicated above, embodiments of the present invention may be used for nondestructive evaluation, Structural Health Monitoring, or quality control monitoring of structures and materials or any combination thereof. Embodiments may also be used for monitoring defects, inclusions, surface properties and misshapes of particles in or adjacent to the chain of granular particles used within the embodiments.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art.

It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . ."

A number of embodiments of the disclosure have been described. Nevertheless, it will be understood that various modifications may be made without departing from the spirit and scope of the present disclosure. Accordingly, other embodiments are within the scope of the following claims.

What is claimed is:

1. An actuation system for applying pulses to a structure or material and/or detecting pulses from a structure or material, the actuation system comprising:
   a holder containing a chain of granular particles;
   a striker structure directing one or more striker particles towards one end of the chain of granular particles; and
   a reloading structure configured to repeatedly engage the one or more striker particles at a lower extant, to lift the one or more striker particles to a selected distance at an upper extant above the chain of granular particles; and to release the one or more striker particles at the upper extant.

2. The actuation system according to claim 1, wherein the reloading structure comprises:
   a dropper structure configured to engage and release the one or more striker particles; and,
   a linear actuator coupled to the dropper structure and configured to move the dropper structure to allow the dropper structure to engage the striker particles at the lower extant and release the one or more striker particles at the upper extant.

3. The actuation system according to claim 1, wherein the striker structure comprises:
   a striker body containing the one or more striker particles;
   a striker piston disposed to engage the one or more striker particles at a first end of the striker piston; and,
   a striker body cap disposed to elastically engage the striker piston via a striker body elastic member at a second end of the striker piston, wherein the second end of the striker piston is opposite the first end of the striker piston.

4. The actuation system according to claim 3, wherein the striker body elastic member comprises one or more springs disposed between the striker body cap and the second end of the striker piston.

5. The actuation system according to claim 3, wherein the striker body cap is configured to be disposed at an adjustable distance from the chain of granular particles and the striker structure further comprises a cap fixing structure configured to hold the striker body cap at a selected distance from the from the chain of granular particles.

6. The actuation system according to claim 5, wherein the cap fixing structure comprises a nut screwed onto the striker body and engaging the striker body cap.

7. The actuation system according to claim 5, wherein the cap fixing structure comprises a cap actuation mechanism engaging the striker body cap and configured to move the striker body cap to a selected distance from the chain of granular particles.

8. The actuation system according to claim 1, wherein precompression is applied to the chain of granular particles.

9. The actuation system according to claim 1, further comprising force sensors detecting forces propagating through one or more particles of the chain of granular particles.

10. The actuation system according to claim 9, wherein the force sensors comprise one or more sensors are disposed within one or more particles of the chain of granular particles.

11. The actuation system according to claim 9, wherein one or more force sensors are coupled to a wired or wireless transmission system.

12. The actuation system according to claim 1, wherein the reloading structure is configured for remote controlling by a wired or wireless connection.

13. An actuation array comprising one or more actuation systems according to claim 1, wherein the one or more actuation systems are controllable to produce a steered actuation pulse beam.

14. A method for repeatedly applying a pulse or series of pulses to a structure or material comprising:
providing a chain of granular particles, wherein a first end of the chain of granular particles is disposed adjacent the structure or material;
moving one or more striker particles to a selected distance from a second end of the chain of granular particles;
launching the one or more striker particles at the chain of granular particles;
engaging the one or more striker particles after the one or more striker particles have been launched at the chain of granular particles and moving the engaged one or more striker particles to the selected distance; and
repeatedly moving, launching, and engaging the one or more striker particles to produce a desired number of pulses or series of pulses.

15. The method according to claim 14, wherein one or more particles in the chain of granular particles contain force sensors.

16. The method according to claim 15, further comprising monitoring data from the force sensors with wired or wireless apparatus.

17. The method according to claim 14, further comprising applying precompression to the chain of granular particles.

18. The method according to claim 14, wherein launching the one or more striker particles and/or engaging the one or more striker particles are remotely controlled by a wired or wireless connection.

19. The method according to claim 14, wherein launching the one or more striker particles comprises striking the one or more striker particles with a spring loaded launching mechanism.

20. The method according to claim 14, further comprising adjusting diameters of one or more particles in the chain of granular particles.

21. The method according to claim 14 further comprising adjusting a speed at which the one or more striker particles are launched at the chain of granular particles.

22. The method according to claim 14 further comprising performing analysis to make one of the following determinations: determine a size or sizes of particles in the chain of granular particles; determine a material or materials for the particles in the chain of granular particles; determine a shape or shapes of particles in the chain of granular particles; determine defects, inclusions or misshapes of a given particle; determine a speed or speeds at which the one or more striker particles are launched at the chain of granular particles; determine a mass or masses of the one or more striker particles; and determine an amount of precompression to be applied to the chain of granular particles.

23. The method according to claim 14 further comprising:
receiving one or more pulses or series of pulses from the structure or material; and,
sensing the one or more pulses or series of pulses with one or more force sensors disposed within one or more particles in the chain of granular particles.

24. The method according to claim 14, further comprising adjusting a force at which the one or more particles are launched at the chain of granular particles.

* * * * *

UNITED STATES PATENT AND TRADEMARK OFFICE
CERTIFICATE OF CORRECTION

| | | |
|---|---|---|
| PATENT NO. | : 8,006,539 B2 | Page 1 of 1 |
| APPLICATION NO. | : 12/364974 | |
| DATED | : August 30, 2011 | |
| INVENTOR(S) | : Damien Eggenspieler et al. | |

It is certified that error appears in the above-identified patent and that said Letters Patent is hereby corrected as shown below:

In column 1, line 22, the following wording should appear:

STATEMENT REGARDING FEDERALLY SPONSORED RESEARCH OR DEVELOPMENT

This invention was made with government support under Grant No. CMMI0825345 awarded by the National Science Foundation. The government has certain rights in the invention.

Signed and Sealed this
Twenty-fourth Day of January, 2012

David J. Kappos
*Director of the United States Patent and Trademark Office*